(12) United States Patent
Fouras (10) Patent No.: US 11,660,059 B2
(45) Date of Patent: *May 30, 2023

(54) APPARATUS AND METHOD OF IMAGING

(71) Applicant: 4DMedical Limited, Melbourne (AU)

(72) Inventor: Andreas Fouras, Woodland Hills, CA (US)

(73) Assignee: 4DMedical Limited, Melbourne (AU)

(*) Notice: Subject to any disclaimer, the term of this patent is extended or adjusted under 35 U.S.C. 154(b) by 142 days.

This patent is subject to a terminal disclaimer.

(21) Appl. No.: 16/857,961

(22) Filed: Apr. 24, 2020

(65) Prior Publication Data

US 2020/0261047 A1 Aug. 20, 2020

Related U.S. Application Data

(63) Continuation of application No. 15/300,367, filed as application No. PCT/AU2015/000219 on Apr. 14, 2015, now Pat. No. 10,674,987.

(30) Foreign Application Priority Data

Apr. 15, 2014 (AU) .............................. 2014901375

(51) Int. Cl.
*A61B 6/00* (2006.01)
*A61B 8/08* (2006.01)
(Continued)

(52) U.S. Cl.
CPC .......... *A61B 6/5217* (2013.01); *A61B 5/7282* (2013.01); *A61B 6/022* (2013.01);
(Continued)

(58) Field of Classification Search
CPC ....... A61B 6/5217; A61B 6/022; A61B 6/032; A61B 6/4014; A61B 6/4085; A61B 6/487;
(Continued)

(56) References Cited

U.S. PATENT DOCUMENTS

| 5,491,642 A | 2/1996 | Wormell et al. |
| 6,373,920 B1 | 4/2002 | Hsieh |

(Continued)

FOREIGN PATENT DOCUMENTS

| DE | 19948827 A1 | 4/2001 |
| EP | 2873371 A1 | 5/2015 |

(Continued)

OTHER PUBLICATIONS

Barker et al. "3-Component Phase-Contrast MRI WSS Vectors in the Carotid Bifurcation are Concurrent with Loca Atherosclerotic Plaque Risk Hypotheses.", Proc. Intl. Soc. Mag. Reson. Med. 18 (2010).

(Continued)

*Primary Examiner* — Chao Sheng
(74) *Attorney, Agent, or Firm* — Loza & Loza, LLP; David S. Sarisky (57) ABSTRACT

A method of imaging motion of an organ that changes volume in a patient including the steps of monitoring change in volume of the organ, and recording multiple in vivo images of the organ, wherein the change of organ volume between the images is constant or of some other predetermined value.

20 Claims, 8 Drawing Sheets

(51) Int. Cl.
*A61B 6/02* (2006.01)
*A61B 6/03* (2006.01)
*A61B 5/00* (2006.01)
*A61B 5/055* (2006.01)

(52) U.S. Cl.
CPC ............ *A61B 6/032* (2013.01); *A61B 6/4014* (2013.01); *A61B 6/4085* (2013.01); *A61B 6/487* (2013.01); *A61B 8/08* (2013.01); *A61B 8/5223* (2013.01); *A61B 5/055* (2013.01); *A61B 6/5288* (2013.01); *A61B 6/541* (2013.01); *A61B 6/542* (2013.01)

(58) Field of Classification Search
CPC ....... A61B 6/5288; A61B 6/541; A61B 6/542; A61B 5/055; A61B 5/7282; A61B 8/08; A61B 8/5223
See application file for complete search history.

(56) References Cited

U.S. PATENT DOCUMENTS

| | | | |
|---|---|---|---|
| 6,385,332 | B1 | 5/2002 | Zahalka et al. |
| 6,549,646 | B1 | 4/2003 | Yeh et al. |
| 6,631,716 | B1 | 10/2003 | Robinson et al. |
| 6,650,928 | B1 | 11/2003 | Gailly et al. |
| 6,816,607 | B2 | 11/2004 | O'Donnell et al. |
| 7,333,643 | B2 | 2/2008 | Murphy et al. |
| 7,376,253 | B2 | 5/2008 | Spreeuwers et al. |
| 7,583,829 | B2 | 9/2009 | Kiraly et al. |
| 7,668,357 | B2 | 2/2010 | Keall et al. |
| 7,742,639 | B2 | 6/2010 | Eck et al. |
| 7,876,936 | B2 | 1/2011 | Raffy |
| 7,985,187 | B2 | 7/2011 | Wibowo et al. |
| 8,090,176 | B2 | 1/2012 | Kinnstaetter et al. |
| 8,175,358 | B2 | 5/2012 | Weese et al. |
| 8,346,342 | B2 | 1/2013 | Kalafut |
| 8,447,380 | B2 | 5/2013 | Kuth et al. |
| 8,483,456 | B2 | 7/2013 | Nagatsuka et al. |
| 8,538,111 | B2 | 9/2013 | Zhang et al. |
| 8,553,832 | B2 | 10/2013 | Camus et al. |
| 8,666,139 | B2 | 3/2014 | Zhang et al. |
| 8,668,652 | B2 | 3/2014 | Wibowo et al. |
| 8,878,838 | B2 | 11/2014 | Hautvast |
| 9,036,887 | B2 | 5/2015 | Fouras et al. |
| 9,044,194 | B2 | 6/2015 | Noji et al. |
| 9,125,621 | B2 | 9/2015 | Nagatsuka et al. |
| 9,198,628 | B2 | 12/2015 | Shimada et al. |
| 9,254,112 | B2 | 2/2016 | Tryggestad et al. |
| 9,289,140 | B2 | 3/2016 | Ross et al. |
| 9,311,702 | B2 | 4/2016 | Pautot |
| 9,760,989 | B2 | 9/2017 | Yin et al. |
| 9,892,513 | B2 | 2/2018 | Gurevich et al. |
| 9,962,086 | B2 | 5/2018 | Dabbah et al. |
| 9,999,401 | B2 | 6/2018 | Korporaal et al. |
| 2004/0092811 | A1* | 5/2004 | Hill ........................ A61B 6/032 600/428 |
| 2005/0053267 | A1* | 3/2005 | Mostafavi ............... G06T 7/254 382/128 |
| 2005/0059876 | A1 | 3/2005 | Krishnan et al. |
| 2005/0113672 | A1 | 5/2005 | Salla |
| 2005/0187464 | A1 | 8/2005 | Ho et al. |
| 2005/0240094 | A1 | 10/2005 | Pinchon et al. |
| 2007/0092864 | A1 | 4/2007 | Reinhardt et al. |
| 2008/0031404 | A1 | 2/2008 | Khamene |
| 2008/0077038 | A1 | 3/2008 | McDonough |
| 2008/0181481 | A1 | 7/2008 | Hong et al. |
| 2008/0193904 | A1 | 8/2008 | Santhanam et al. |
| 2008/0269592 | A1 | 10/2008 | Kuth |
| 2009/0003511 | A1 | 1/2009 | Roy et al. |
| 2009/0207968 | A1 | 8/2009 | Grass |
| 2009/0208084 | A1 | 8/2009 | Liu et al. |
| 2009/0252394 | A1 | 10/2009 | Liang et al. |
| 2010/0041992 | A1 | 2/2010 | Ohuchi et al. |
| 2010/0063410 | A1 | 3/2010 | Avila |
| 2010/0191131 | A1 | 7/2010 | Revishvili et al. |
| 2010/0228143 | A1 | 9/2010 | Teschner |
| 2011/0051885 | A1 | 3/2011 | Buelow et al. |
| 2012/0041318 | A1 | 2/2012 | Taylor |
| 2013/0046176 | A1 | 2/2013 | Mistretta et al. |
| 2013/0070062 | A1 | 3/2013 | Fouras et al. |
| 2014/0192952 | A1 | 7/2014 | Keall et al. |
| 2015/0320325 | A1 | 11/2015 | Sheehan et al. |
| 2016/0095580 | A1 | 5/2016 | Rubin |

FOREIGN PATENT DOCUMENTS

| | | |
|---|---|---|
| EP | 2299286 B1 | 9/2020 |
| JP | 2007089674 A | 4/2007 |
| JP | 2010046212 A | 3/2010 |
| KR | 10-2004-006584 A | 7/2004 |
| WO | 2006116178 A1 | 11/2006 |
| WO | 2008085048 A1 | 7/2008 |
| WO | 2011017739 A1 | 2/2011 |
| WO | 2011032210 A1 | 3/2011 |
| WO | 2012026145 A1 | 3/2012 |
| WO | 2013053000 A1 | 4/2013 |
| WO | 2013155556 A1 | 10/2013 |
| WO | 2014143974 A1 | 9/2014 |
| WO | 2015157799 A1 | 10/2015 |

OTHER PUBLICATIONS

Brahme et al. "4D laser camera for accurate patient positioning, collision avoidance, image fusion and adaptive approaches during diagnostic and therapeutic procedures.", Int'l J. Physics Research & Practice. vol. 35:5 (May 2008).

Choi et al. "Numerical study of high-frequency oscillatory airflow and convective mixing in a CT-based human airway model.", Annals Biomed. Engr. vol. 38:12, pp. 3550-3571 (Dec. 2010).

Christensen et al., "Tracking lung tissue motion and expansion/compression with inverse consistent image registration and spirometry.", Int'l J. Med. Phys. Res.and Practice, vol. 34:6, Part 1 (first published May 21, 2007).

Cui et al., "Fluoroscopic gating without implanted fiducial markers for lung cancer radiotherapy based on support vector machines.", Phys Med Biol, 53:N315-27 (2008).

Docef et al. "Deformed CT reconstruction from limited projection data.", Int'l. Congress Series, vol. 1281, pp. 104-108 (May 2005).

Dubsky et al. "Three component, three dimensional X-ray particle image velocimetry using multiple projections.", 14th Int Symp on Applications of Laser Techniques to Fluid Mechanics, Lisbon, Portugal (Jul. 7-10, 2008).

Dubsky et al. "Computed tomographic x-ray velocimetry for simultaneous 3D measurement of velocity and geometry in opaque vessels.", Experiments in Fluids vol. 52:3 pp. 543-554 (Mar. 2012).

Dubsky et al. "Synchrotron-based dynamic computed tomography of tissue motion for regional lung function measurement.", J. Royal Soc. Interface https://doi.org/10.1098/rsif.2012.0116 (Apr. 4, 2012).

Fouras et al. "Three-dimensional synchrotron x-ray particle image velocimetry", J. Applied Physics 102 064916 (Sep. 28, 2007).

Fouras, et al. "The past, present, and future of x-ray technology for in vivo imaging of function and form.", J. Applied Physics. 105, 102009 (2009).

Fouras et al. "In-vivo Synchrotron PIV for the measurement of airway motion.", 8th Int'l Symposium on Particle Image Velocimetry—PIV09 Melbourne Victoria Australia (Aug. 25-28, 2009).

Fouras et al. "Engineering imaging: using particle image velocimetry to see physiology in a new light.", Clinical & Experi. Pharmacology and Physiology 36,238-247 (2009).

Guerrero et al. "Dynamic ventilation imaging from four-dimensional computed tomography.", Physics in Medicine & Biology, vol. 51:4 (Jan. 25, 2006).

Irvine, et al. "Phase retrieval for improved three-dimensional velocimetry of dynamic x-ray blood speckle.", Appl. Phys. Lett. 93, 153901 (Oct. 15, 2008).

Kim et al. "X-ray PIV measurements of blood flows without tracer particles.", Experiments in Fluids, vol. 41:2, pp. 195-200 (Aug. 2006).

(56) References Cited

OTHER PUBLICATIONS

Lu et al. "Blood flow velocity and ultra-filtration velocity measured by CT imaging system inside a densely bundled hollow fiber dialyzer.", Int'l J. of Heat and Mass Transfer. vol. 53:9-10, pp. 1844-1850 (Apr. 2010).
Rodriguez-Romero, et al. "The influence of respiratory motion on CT image volume definition.", Int. J. Med. Phys. Res. & Practice vol. 41:4 (Mar. 7, 2014).
Simon, "Regional ventilation and lung Mechanics Using X-Ray CT1.", Academic Radiology vol. 12:11, pp. 1414-1422 (Nov. 2005).
Soussen et al. "Polygonal and polyhedral contour reconstruction in computed tomography.", IEEE Transactions on Image Processing, vol. 13:11 (Nov. 2004).
Frangi et al. "Multiscale vessel enhancement filtering." Proc. 1998 MICCAI Int'l Conf. on Medical Image Computing and Computer-Assisted Intervention, Cambridge, Mass., 8 pp. (Oct. 11, 1998).
Wiepütz et al. "Simultaneous Assessment of Airway Instability and Respiratory Dynamics with Low-Dose 4D-CT in Chronic Obstructive Pulmonary Disease: A Technical Note." Respiration 87:294-300 (2014).
Wong et al. "Cardiac flow component analysis.", Medical Engr. & Physics vol. 32:2 pp. 174-188 (Mar. 2010).
Yin et al., "Simulation of pulmonary air flow with a subject-specific boundary condition.", J. Biomechanics vol. 43:11, pp. 2159-2163 (Aug. 10, 2010).
Zhang et al. "Evaluation of segmentation algorithms for vessel wall detection in echo particle image velocimetry.", IEEE Int'l Ultrasonics Symposium (DOI: 10.1109/ULTSYM.2009.5441630) (Sep. 20, 2009).
Jimenez-Carretero et al. 3D frangi-based lung vessel enhancement filter penalizing airways. Proc. 2013 IEEE 10th International Symposium on Biomedical Imaging, San Francisco, CA, 4 pages (Apr. 7, 2013).
Orkisz et al. "Segmentation of the pulmonary vascular trees in 3D CT images using variational region-growing." IRBM, vol. 35:1, pp. 11-19 (Feb. 2014).
Qian et al. "A non-parametric vessel detection method for complex vascular structures." Medical Image Analysis, vol. 13, Issue 1, pp. 49-61 (Feb. 2009).
Rudyanto et al. "Quantification of pulmonary vessel diameter in low-dose CT images." Proceedings vol. 414 Medical Imaging 2015, Computer-Aided Diagnosis Orlando, Florida, 6 pages (Feb. 21, 2015).
Sato et al. "TEASAR: Tree-structure extraction algorithm for accurate and robust skeletons." Proc. 8th Pacific Conf. on Computer Graphics and Applications, Hong Kong, China, pp. 281-449 (2000).
Schindelin et al. "Fiji—an Open Source platform for biological image analysis." Nature Methods, vol. 9, No. 7, 15 pp. (Jun. 28, 2012).
Soria et al. "Accuracy of out-of-plane vorticity component measurement using in-plane velocity vector field measurements." 12th Australasian Conference on Fluid Mechanics, Univ. Sydney, Australia (Dec. 10, 1995).
Staring et al. "Pulmonary vessel segmentation using vessel enhancement filters." Grand Challenge Website, available online at https://grand-challenge.org/site/VESSEL 12/Results/ insertresults/ public/20120328103241_163_LKEBChina_ VESSEL 12_StrainEnergy/algorithm_description.pdf (Jan. 2012).
Sun et al. "Detection of central pulmonary embolism on non-contrast computed tomography: a case control study." Int'l J. Cardiovascular Imaging, vol. 30, No. 3, 8 pages (Mar. 2014).
Wittram et al. "CT Angiography of Pulmonary Embolism: Diagnostic Criteria and Causes of Misdiagnosis." RadioGraphics vol. 24, No. 5, 20 pp., (Sep. 1, 2004).
Thurgood et al. "Functional lung imaging during HFV in preterm rabbits." PLOS One; https://doi.org/10.1371/journal.pone.0048122 (Oct. 30, 2012).
PCT/AU2013000390. Int'l Prelim. Report on Patentability (dated Oct. 21, 2014).
PCT/AU2012/001225 Int'l Prelim. Report on Patentability (dated Apr. 15, 2014).
PCT/AU2017/000054. Int'l Search Report (dated Jun. 22, 2017).
PCT/AU2018000028. Int'l Search Report & Written Opinion (dated Jun. 8, 2018).
PCT/AU2015/000219 Int'l Search Report (dated Jun. 4, 2015).

\* cited by examiner

APPARATUS AND METHOD OF IMAGING

CROSS-REFERENCE TO RELATED APPLICATIONS

This application is a continuation of U.S. patent application Ser. No. 15/300,367, filed Sep. 29, 2016, now U.S. Pat. No. 10,674,987, which is a U.S. national stage application of and claims priority to International Application No. PCT/AU2015/000219, filed on Apr. 14, 2015, which claims the benefit of Australian Application No. 2014901375, filed on Apr. 15, 2014, the entire disclosures of which are incorporated herein by reference.

TECHNICAL FIELD

The present invention relates to the field of imaging, particularly imaging of organs such as the lung.

In one form, the invention relates to the field of imaging organs, such as the lung for diagnostic or research purposes.

In one particular aspect the present invention is suitable for use as a technique for assessing organ motion.

It will be convenient to hereinafter describe the invention in relation to human medical applications however, it should be appreciated that the present invention is not limited to that use only and could, for example, be used for veterinary applications.

Furthermore, it will be also convenient to hereinafter describe the invention in relation to CTXV (e.g., see U.S. Pat. No. 9,036,877), however it should be appreciated that the present invention is not limited to that imaging technique and could, for example be used with other forms of imaging including X-ray computer tomography (CT), particularly 4D-CT, fluoroscopy, MRI, ultrasound or any other imaging method that acquires multiple images over time.

BACKGROUND

It is to be appreciated that any discussion of documents, devices, acts, or knowledge in this specification is included to explain the context of the present invention. Further, the discussion throughout this specification comes about due to the realization of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

In the past, X-ray CT has been extensively used in radiography to investigate the anatomy and function of the lungs. CT uses computer processed X-rays to produce tomographic images (virtual 'slices') of specific areas of a lung. Digital geometry processing is used to generate a three-dimensional image of the inside of the lung from a series of two-dimensional radiographic images taken around a single axis of rotation.

X-ray slice data is generated using an X-ray source that rotates around the object in a circular shroud. X-ray sensors are positioned on the opposite side of the circle from the X-ray source. Early versions of the imaging machines operated by rotating the X-ray source and detectors around a stationary patient. Following each complete rotation, the patient would be moved axially and the next rotation carried out. Newer machines have been designed to allow continuous rotation of the X-ray source and detectors while the patient is slowly and smoothly slid through the X-ray circular shroud. These are called helical or spiral CT machines.

CT can be used for imaging most body structures. It is particularly useful for detecting both acute and chronic changes of structure inside the lungs. These changes may not be detectable using conventional two-dimensional X-ray imaging. A variety of techniques are used. For example, evaluation of chronic interstitial processes such as emphysema or fibrosis is carried out by taking thin slices of data and applying high spatial frequency reconstructions.

One of the principal limitations of these approaches is the need to image the lung while it is stationary in order to minimize blurring. In particular, CT has poor temporal resolution limiting its use for a dynamic lung test. CT scanning is typically performed at two different time intervals—upon breath hold at inspiration or expiration—usually minutes apart.

This has obvious drawbacks and limits the ability of CT to be used for dynamic lung function testing. Specifically, it produces a sampling of the lung and an interpolation is required to deduce lung motion between the two steady state conditions, but such methods assume that the motion follows a linear or defined path. They cannot produce continuous real-time images that would provide information regarding lung motion and be used to detect diseases that cause subtle changes in lung structure or function.

With the advent of fast CT scanning, it has been possible to develop methods called 4D-CT that capture images over time to depict movement of body organs, such as inflation and deflation of a lung. A typical 4D-CT scan involves 10 to 50 rotations around the patient, each coordinated with the table moving through the circular shroud. Fast scanning can be carried out at a rate of about 4 rotations/sec, with the detector taking about 1000 'snapshots'/rotation. Each 'snapshot' is carried out at one position (angle or 'projection') of the X-rays source. Typically between 40,000 to 200,000 images are collected in a 4D-CT.

For example, 4D-CT has been used for measurement of lung function, including expansion using traditional absorption based imaging, but has the drawback of delivering significant levels of radiation dose to the patient. Visualizing, controlling, and tracking patient specific respiratory motion is key to more precisely targeted irradiation treatment for disorders such as chest and abdominal cancers that move with the diaphragm. Motion of cancers causes problems with irradiation treatment because moving targets may appear with distorted shapes and in wrong locations on CT images. In order to compensate for this, larger irradiation fields and concomitant large radiation doses are used to ensure that the tumor is not missed.

Accordingly, respiratory gating may be combined with the 4D-CT for treating 'moving' tumors such as lung tumors. One approach is through the use of a small "box" placed on the patient's chest/upper abdomen and specialized cameras are used to monitor the motion of this box during respiration. This information is used to correlate the position of the lung tumor with specific phases of the respiratory cycle. At treatment, motion of the box allows the treatment beam to be turned on and off (gating) during specific phases of the breathing cycle. (Jiang S B et al, Int J Radiat Oncol Biol Phys 2008; 71:S103-7; Phys Med Biol 2008; 53:N315-27).

Use of CT has increased dramatically over the last two decades. An important issue within radiology today is how to reduce the radiation dose during CT scanning without compromising the image quality. In general, higher radiation doses result in higher-resolution images, while lower doses lead to increased image noise and blurred images. However, higher radiation doses increase adverse side effects, including the risk of radiation induced cancer.

In the past, attempts have been made to reduce exposure to ionizing radiation during a CT scan including:

1. new software technology to more effectively utilize the data recorded at the detector, 2. individualizing the scanning and adjusting the radiation dose to the body type and body organ examined, and 3. evaluating the appropriateness of avoiding CT scanning in favor of another type of examination.

Notwithstanding these efforts, the relatively high radiation dose imposed on a patient by a CT scan (especially by a 4D-CT scan), is a key problem acting against the increased use of CT. In addition to CT, there are many other forms of imaging capable of dynamic imaging of dynamic biological processes, such as breathing.

The fluoroscope is ideally suited to dynamic imaging of the thorax and is used in a wide range of procedures such as barium swallow examinations, cardiac catheterization, arthrography, lumbar puncture, placement of intravenous (IV) catheters, intravenous pyelogram, hysterosalpingogram, and biopsies including bronchoscopy. Fluoroscopy may be used alone as a diagnostic procedure, or may be used in conjunction with other diagnostic or therapeutic media or procedures.

One specific application of the fluoroscope, and related medical imaging configurations, is in the acquisition of dynamic sequences for CTXV analysis. CTXV analysis is possible from acquisition sequences including (but not limited to): multiple images acquired from multiple perspectives (projections); multiple images acquired from a number of perspectives (projections) simultaneously; and, continuous acquisition with a moving perspective.

The work of Keall et al (US20140192952) attempts to reduce the clustering of projections that occurs when gating to a respiratory signal and using a constant rotation speed in 4DCBCT. To avoid this clustering of projections and achieve an even distribution of projections around the subject, Keall changes two variables: (1) the rotation speed of the gantry and (2) the time interval between projections.

With the advent of advanced imaging systems such as those used in CTXV and advances with 4D-CT technologies, fast imaging rates are achievable. These higher rates of image acquisition allow for more complex timing of when images are acquired throughout a dynamic event. This increased speed of acquisition allows for enhanced temporal resolution of rapidly occurring dynamic processes or events.

Accordingly there is an ongoing need to improve the quality of information derived from scanning without increasing, or preferably decreasing patient radiation exposure.

In the field of imaging based motion analysis, a key parameter that affects the image quality and dynamic range of the measurement is the magnitude of the sample's displacement that occurs between sequential images. This will be determined by the speed of the sample and the rate of acquisition. If the sample displacement is too large or too small, the measurement quality will be degraded. Imaging of samples that exhibit a large range of speeds during the measurement sequence using a constant acquisition rate will therefore inevitably cause degraded measurement quality for some of the frames.

In the field of imaging based motion analysis there are several techniques that are commonly employed to improve the quality of the motion measurement or the dynamic range of the measurements. One such example is the use of a 'frame skip' in a PIV (particle image velocimetry) analysis. This is where the image analysis compares images that are more than 1 image apart. As such the optimum signal to noise can be obtained for slower particles that have a very small displacement between sequential images.

When using X-ray images as the input, techniques such as these result in an increase in radiation dose imparted to the subject as extra (redundant) images are acquired. In X-ray imaging, extra images equate to extra dose delivered to the subject. Therefore for motion measurement from X-ray images, such as in a CTXV analysis, other techniques must be employed to overcome this.

SUMMARY

An object of the present invention is to provide improved techniques for assessing lung function and diagnosing lung conditions.

Another object of the present invention is to provide improved technology for obtaining data of lung motion.

A further object of the present invention is to alleviate at least one disadvantage associated with the related art.

It is an object of the embodiments described herein to overcome or alleviate at least one of the above noted drawbacks of related art systems or to at least provide a useful alternative to related art systems.

In a first aspect of embodiments described herein there is provided a method of imaging motion of an organ in a patient including the steps of: monitoring a parameter corresponding to motion of the organ, and acquiring multiple in vivo images of the organ, wherein the timing of image acquisition is correlated with a predetermined change in parameter value.

Where used herein the term 'organ' is intended to refer to any collection of tissues joined in a structural unit to serve a common function, or part thereof, and includes the heart, lungs, and blood vessels. In a particularly preferred embodiment the organ comprises one or both lungs or lobes thereof.

The aforesaid correlation may be direct, or indirect correlation.

In a more specific aspect of the aforesaid embodiment there is provided a method of imaging motion of an organ that changes volume in a patient including the steps of: monitoring change in volume of the organ, and acquiring multiple in vivo images of the organ, wherein the timing of image acquisition is correlated with change of organ volume between the images.

Preferably the change in parameter value between images is a predetermined value, which may be constant or varied over time. More preferably the predetermined value is a constant value. The parameter value relates to change in any one or any combination of shape, volume, flow, pressure, shear, displacement, temperature, color, orientation, or location of the organ. In a particularly preferred embodiment the parameter value is volume.

Further to this, it will be appreciated by a person skilled in the art, that flow may be integrated to provide volume information and volume may be differentiated to provide flow information. As such either flow or volume signals can be considered to contain the same information.

Pressure is a related parameter to flow and volume, and pressure has the advantage of being a simpler and more common measure that is clinically made. In one embodiment of the present invention, pressure alone is used as a direct physiological measure and to this trigger the imaging system.

When the organ being imaged is the lung, lung tissue motion or displacement may be measured from many means including imaging methods such as those discussed throughout this disclosure. Measurements of lung tissue motion allow for accurate optimization of the desired signal timing when used for a motion analysis of the lungs, thus allowing a real-time feedback system.

Measurements of chest wall displacement are also related to the displacement of lung tissue and in particular a change in lung volume. Chest wall displacement may be measured from a number of techniques including laser-based grids projected onto the subject, markers placed on the subject and stereo video techniques. Measuring the chest wall displacement can often have the advantage of not requiring any equipment to contact the patient. It will be appreciated by a person skilled in the art that many other physiological measurement techniques and many other physiological parameters can be used to infer information of the displacement or volume change of lung tissue.

In the past, images of organs that change volume, such as the heart, blood vessels or lungs have been recorded at a constant imaging rate—typically the fastest possible or at a rate sufficient to capture the most rapidly occurring dynamic event. For systems where events are not occurring at a constant rate, the desired temporal resolution (in a relative sense) is not constant, potentially leading to an excess of captured images. An excess of images may correlate to an increase of cost for analysis, review, and storage of those images. In the case of X-ray imaging systems, an excess of images results directly results in an excess of X-ray dose. In the case of the lungs, this leads to a large proportion of images being captured at the end of inspiration and the end of expiration where very little change in the lung occurs, with only a small proportion of images being captured at the most transient moments, being during peak inspiratory flow or peak expiratory flow.

Specifically in the case of CTXV imaging the accuracy of the airflow measurements is a function of the change in volume of the system over the imaging period. Small changes in volume over a measurement period may result in large errors relative to the signal. Large changes in volume over a measurement period may result in large errors due to inadequate temporal resolution of non-linear phenomena. Similarly, large errors may result from sub-optimal cross-correlations that result from a large volume change over the measurement period.

By contrast, the method of the present invention, is directed to optimizing the quantification possible from dynamic imaging sequences. It is expected that this approach will minimize the number of images captured outside of times of most rapid change, concomitantly minimizing the dosage of radiation to the subject. In the case of measuring airflow within the lungs, the method of the present invention allows the optimization of the imaging sequence, both minimizing airflow measurement errors and X-ray dose.

The change of organ volume may be monitored by any convenient means, including measurement of another directly related physiological parameter, such as airflow or blood pressure. These include, in the case of lungs, airflow at the mouth, spirometry, chest wall measurements using a laser generated grid or image, or a band around the thorax, or fitting to standard respiration curves. In the case of the heart or blood vessels they can include measurements of blood pressure or blood flow. It will be readily apparent to the person skilled in the art that the change of organ volume is not limited to these methods and many other monitoring means could be used. For instance, when imaging the heart, using an ECG to infer the temporal variations of blood volume may be used.

In a second aspect of embodiments described herein there is provided a method of imaging motion of an organ in a patient including the steps of: monitoring change in a parameter corresponding to motion of the organ, such as change of volume of the organ to create monitoring data that is fed in real time to an imaging control system, and acquiring multiple in vivo images of the organ in response to an actuation signal from the control system, wherein the timing of image acquisition is correlated with predetermined change in parameter value.

Typically the predetermined change in parameter value is varied over time, or alternatively is constant. The collection of images corresponding to a constant or other predetermined parameter change of an organ may be achieved by any convenient means.

In one preferred embodiment, images may be collected when the organ changes volume by a predetermined amount by use of HV switching of the kV generator, or shuttering the X-ray source/detector, or by altering the manner in which a radiation beam impinges on the target organ, or other triggering means.

In another aspect of embodiments described herein there is provided an application to collect images according to the method of the present invention, said application comprising a predetermined instruction set for initiating recordal of images that correspond to a predetermined change of organ volume.

In a further aspect, the method of the present invention may include the step of measuring a data field of organ motion between two or more of the acquired images.

The acquisition of images according to the present invention may be carried out from multiple perspectives. In a particularly preferred embodiment the multiple in vivo images are recorded from two or more perspectives, each image comprising encoded data, and a spatial velocity data field of organ motion is reconstructed from the encoded data.

In another embodiment of the method of the present invention, the method further includes monitoring change in the parameter to create monitoring data that is fed in real time to an imaging control system, and acquiring multiple in vivo images of the organ comprising encoded data from a first perspective in response to an actuation signal from the control system, acquiring multiple in vivo images of the organ comprising further encoded data from at least one further perspective in response to an actuation signal from the control system, and subsequently, reconstructing a spatial velocity data field of organ motion from the encoded data.

In yet a further aspect of embodiments described herein there is provided, in an apparatus comprising: (i) one or more energy source; (ii) one or more detectors for acquiring images created by energy from the one or more energy sources passing through a subject intermediate the energy source and detector; and a signal processing unit comprising a sensor to monitor the change in volume of the organ, the output of the sensor being analyzed to provide an input to trigger the timing of image acquisition in accordance with the present invention.

In another aspect of embodiments described herein there is provided a computer readable storage medium for storing in non-transient form an application to enable monitoring, acquiring images and timing according to the method of the present invention.

In a yet further aspect of embodiments described herein there is provided an application stored on non-transitory medium adapted to enable imaging, said application comprising a predetermined instruction set adapted to enable a method according to method of the present invention.

The person skilled in the art will appreciate that the method of the present invention can be used in conjunction with any well known imaging technique. Preferably the imaging of motion according to the present invention is carried out using an imaging method chosen from the group comprising computer tomographic X-ray velocimetry, computer tomography, cone-beam computer tomography, fluoroscopy, magnetic resonance imaging or ultrasonography.

The patient may be human or another animal and the present invention is thus useful for a range of human and veterinary applications in the fields of diagnostics and research.

Other aspects and preferred forms are disclosed in the specification and/or defined in the appended claims, forming a part of the description of the invention.

In essence, embodiments of the present invention stem from the realization that the existing time based paradigm of imaging is not suitable for organs that move, especially when in a non-linear fashion, when an analysis of the motion of the organ is carried out. In the case of the lung, it maximizes collection of images during periods of greatest diagnostic interest in terms of motion and minimizes collection of images during periods of least diagnostic interest in terms of motion.

By dispensing with the existing paradigm of imaging based on time, significant advantages are provided by the present invention including the following: collection of images is maximized at times when the most useful information can be obtained and minimized at other times, improving efficiency of data collection and quality of motion analysis, improvement in functional motion data available for clinical diagnosis and treatment, data collection and storage is reduced compared to conventional imaging, improving computing efficiency, patient radiation dosage is minimized, lower operating power can be used for scanners, reducing required cooling times and increasing patient throughput and overall economy.

One embodiment of this technique aims to cluster the images into each projection, by taking multiple images from each view. This then allows for a calculation of motion from each aforesaid view and therefore a reconstruction of the full 4D motion field of the lungs. Techniques for image reconstruction such as CT, 4DCT and 4DCBCT aim to distribute the projections evenly around the patient from a large number of views.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which.

DETAILED DESCRIPTION

Figure 1A:
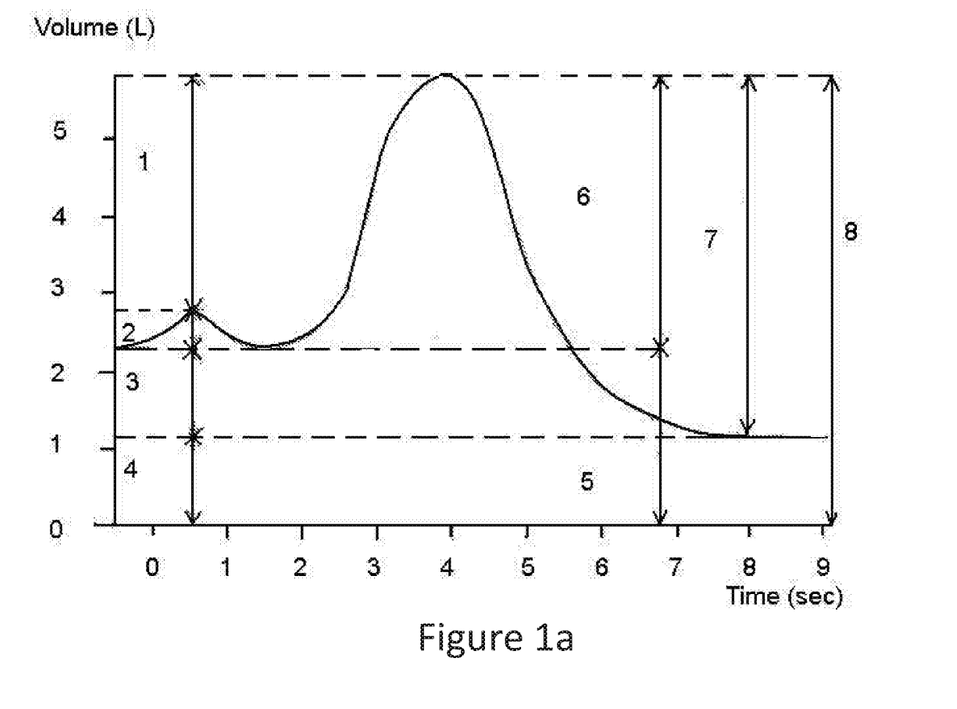
FIGS. 1a and 1b illustrate lung inspiration and expiration by plots of lung volume against time (sec) (FIG. 1a, also referred to herein as FIG. 1a) and lung air pressure (cm/$H_2O$) versus time (sec) (FIG. 1b, also referred to herein as FIG. 1b).

FIG. 1a is a plot of lung volume (liters) versus time (sec) during inspiration and expiration of a human lung. The plot illustrates inspiratory reserve volume (IRV) 1, VT 2, expiratory reserve volume (ERV) 3, residual volume (RV) 4, functional reserve capacity (FRC) 5, inspiratory capacity (IC) 6, vital capacity (VC) 7, total lung capacity (TLC) 8

Figure 1B:
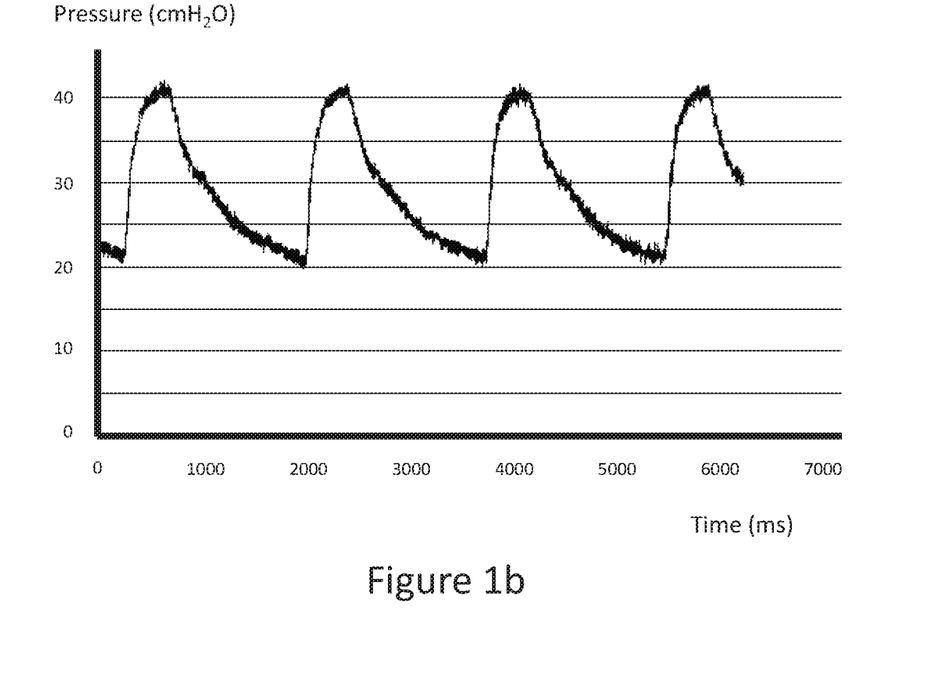

FIG. 1b is a plot of pressure (cm/$h_2O$) versus time (ms) for inspiration and expiration of a human lung. The flow of air into and out of the lung can be correlated with the change in volume of the lung as shown in FIG. 1a.

In the past, images of organs that change volume, such as the heart, blood vessels or lungs have been recorded at the fastest imaging rate possible with a constant time between images.

Figure 3A:
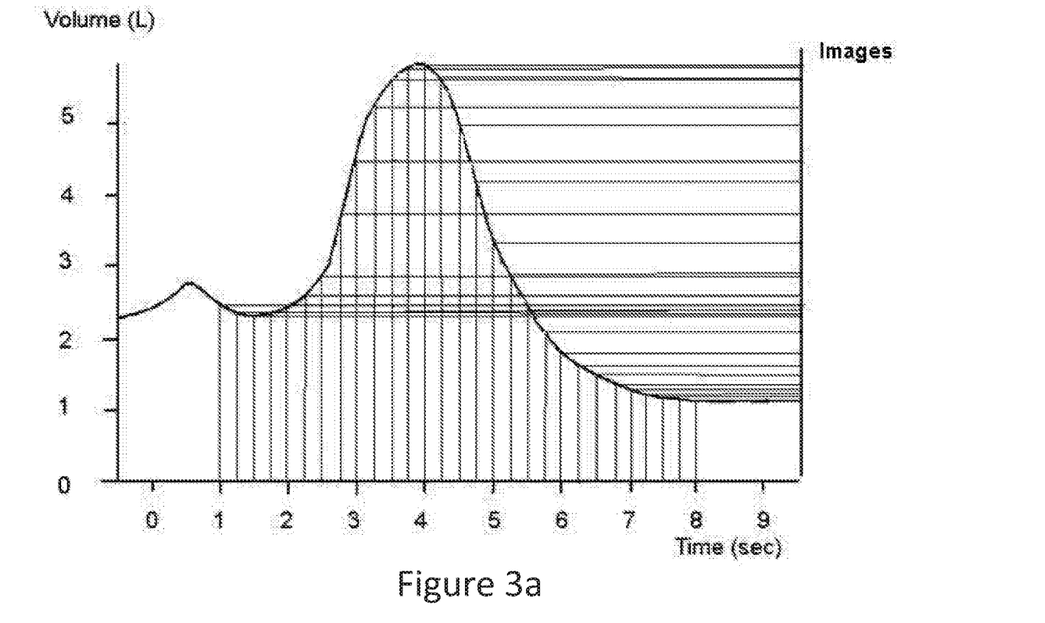
FIGS. 3a and 3b are plots of lung volume against time as shown in FIG. 1a, marked up to indicate a scanning regime according to the prior art during inspiration and expiration (FIG. 3a, also referred to herein as FIG. 3a) and during expiration alone (FIG. 3b, also referred to herein as FIG. 3b).
Figure 3B:
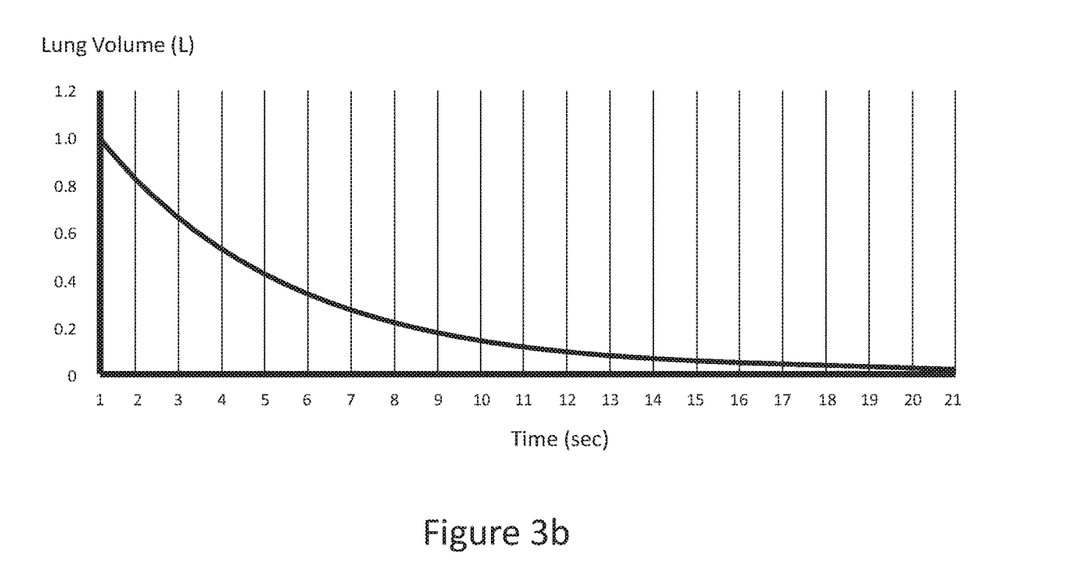

With reference to lungs, this was an attempt to capture the fast motion that occurs during the beginning of the inspiratory cycle and the beginning of the expiratory cycle. FIG. 3 is a plot of lung volume (liters) against time (sec) that illustrates sequential scanning according to the prior art technique during inspiration and expiration (FIG. 3a) and during expiration only (FIG. 3b) with a constant time period between each image.

However, as illustrated in FIG. 3a, this will result in many images being captured during the end of inspiration and expiration where the volume (and pressure) curves have begun to asymptote towards their final values and little lung motion is actually happening.

Figure 2A:
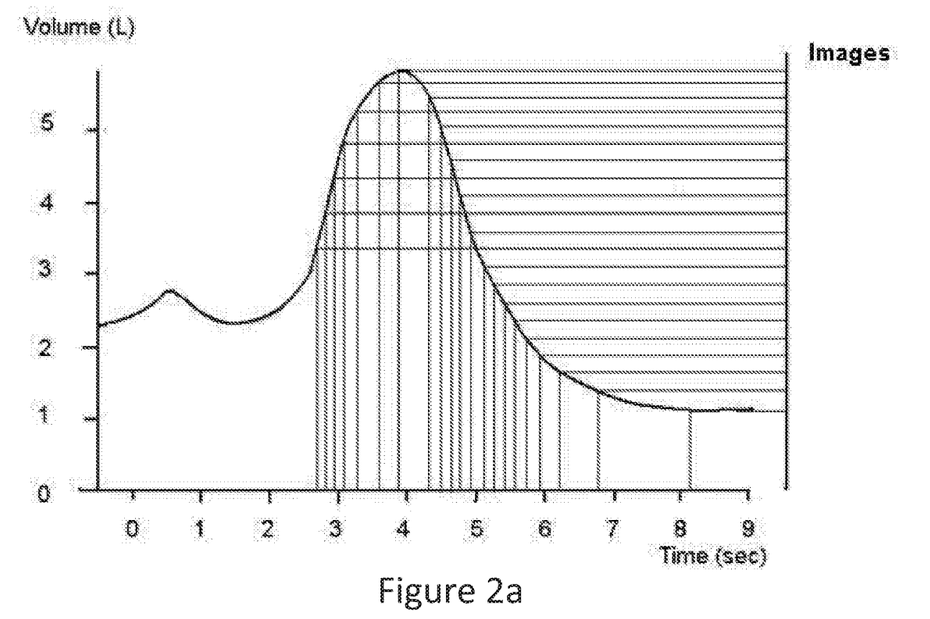
FIGS. 2a and 2b are plots of lung volume against time as shown in FIG. 1a, marked up to indicate a scanning regime according to the present invention during inspiration and expiration (FIG. 2a, also referred to herein as FIG. 2a) and during expiration alone (FIG. 2b, also referred to herein as FIG. 2b).
Figure 2B:
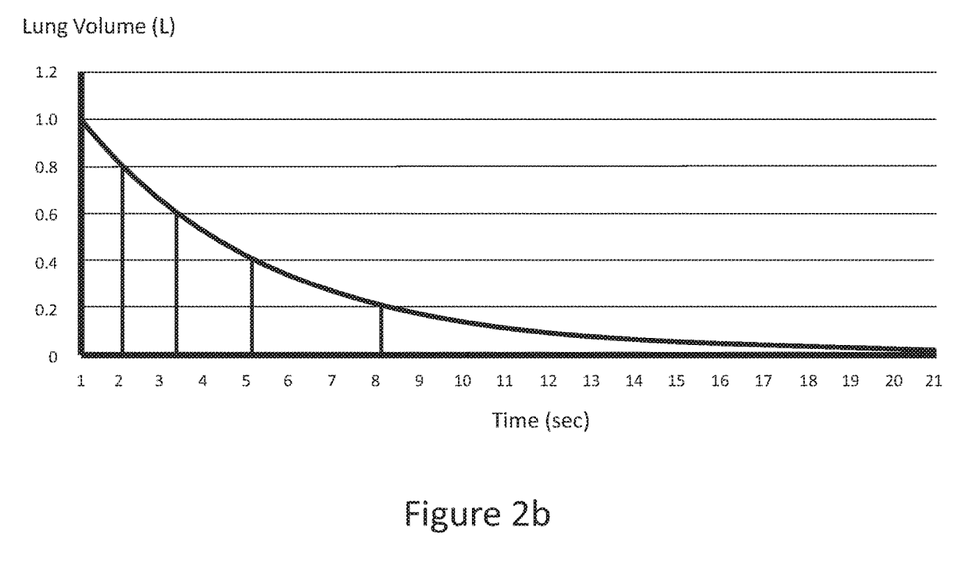

By contrast, FIG. 2 illustrates volume based gating for scanning according to the present invention with a constant lung volume change between each image. FIG. 2 is a plot of lung volume against time during inspiration and expiration (FIG. 2a) and during expiration alone (FIG. 2b). Thus, for a predetermined unit of air flow or change in lung volume, a predetermined number of images can be taken. This optimizes the proportion of images taken during the course of inspiration and expiration when the lung is working hardest and the most information regarding its health can be obtained. It also minimizes the number of images taken at other times, such as the end of inspiration and expiration when the lung is not working as hard, concomitantly minimizing the dosage of radiation.

The method of the present invention does not require images to be taken as fast as possible at over-power levels. Instead, using the method of the present invention the CTXV scanner can be run at a lower power level without the need to cool-down, or for a shorter cool-down period. This allows more efficient throughput of patients, lower power usage, and thus overall better economy of usage of a CTXV scanner.

Figure 4:
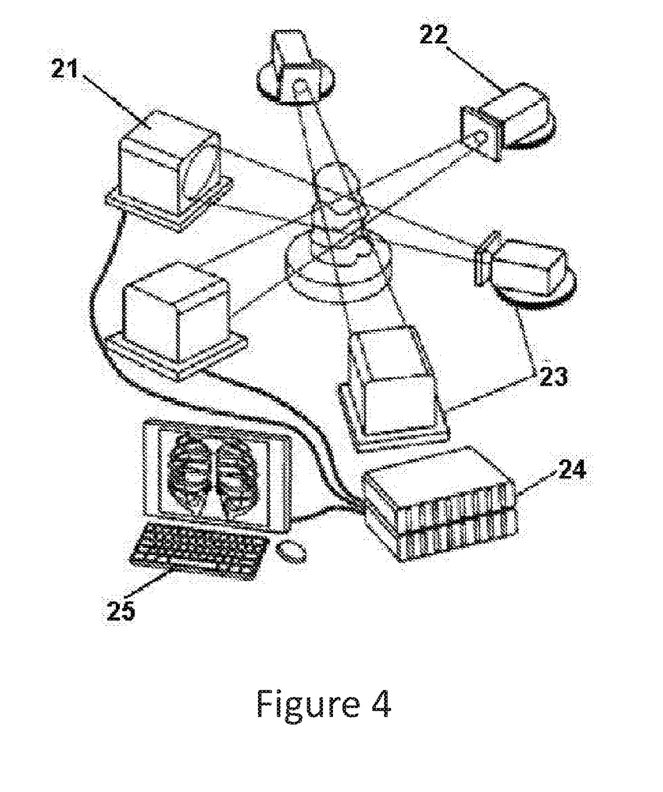
FIG. 4 illustrates a typical arrangement of components in a CTXV scanner.

The current invention is particularly valuable when used in CTXV imaging and CTXV scanners of the prior art as depicted in FIG. 4. FIG. 4 is a schematic diagram outlining the basic design of a CTXV system according to the present invention. The diagram shows three polychromatic X-ray beams transmitted through a sample and converted to visible light by scintillators. High-speed detector systems then produce a set of images. Multiple projection data are gathered simultaneously without rotating the sample. Coordinates (typically Cartesian co-ordinates (x, y, z)) are fixed to the sample and rotated at an angle θ from the beam axis p. With reference to FIG. 4, each imaging line would typically consist of the following key components:

a. video speed or double shutter X-ray camera (21);
b. cone beam X-ray source (22);
c. source modulation system (23);
d. basic source alignment hardware (24a);
e. high-resolution camera alignment hardware (24b);
f. image capture and analysis hardware (25); and
g. user interface (26).

Figure 5A:
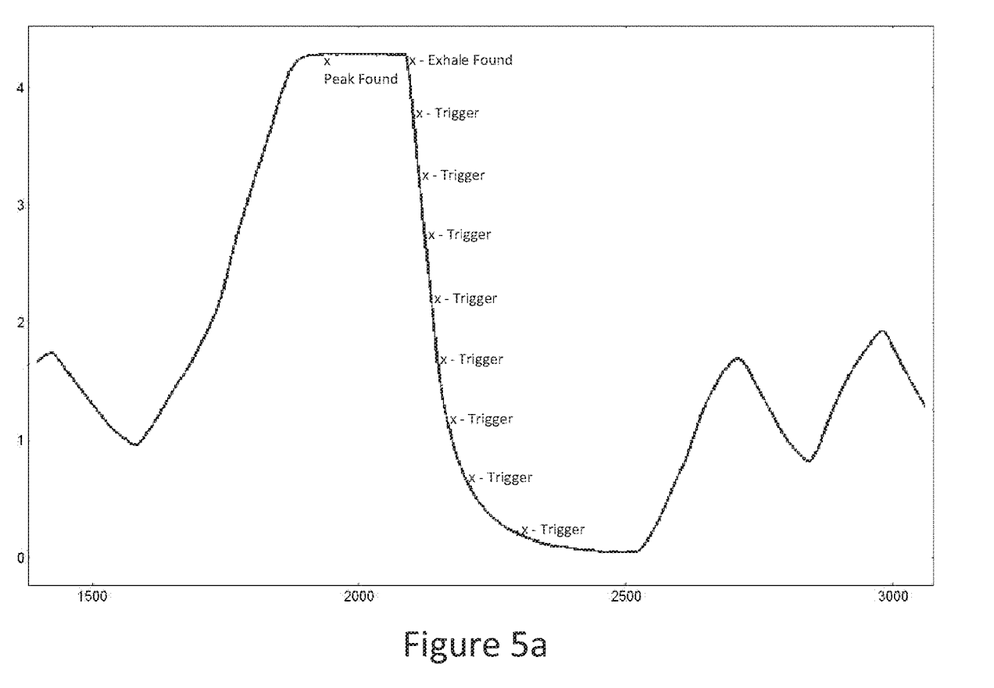
FIGS. 5a and 5b illustrate the output from the application as it detects when to trigger the imaging system based on a constant and preset change of volume (FIG. 5a, also referred to herein as FIG. 5a) and the non-linear time base is depicted on a subset of the same data (FIG. 5b, also referred to herein as FIG. 5b).
Figure 5B:
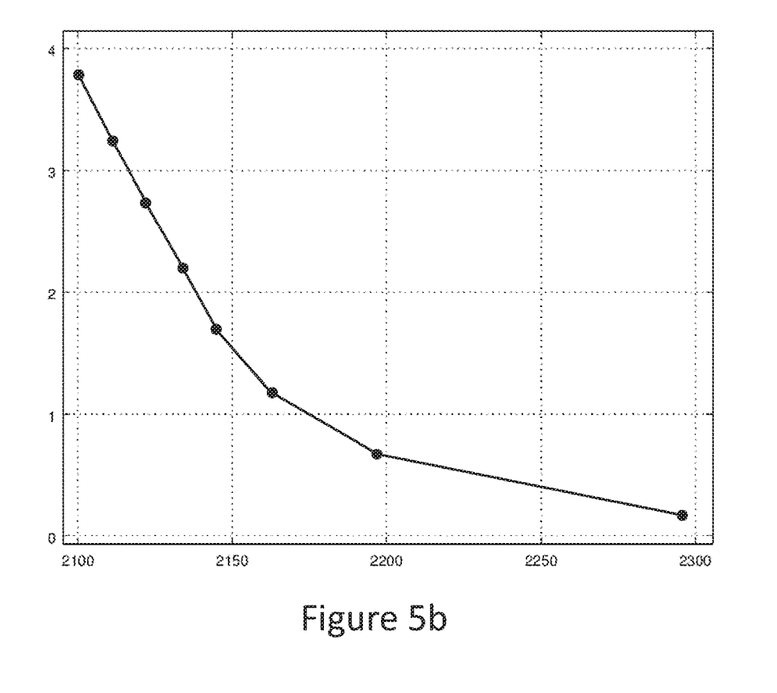

FIG. 5 shows an actual volume vs time graph captured from a subject. The points chosen to trigger for image acquisition correlates to an equal volume spacing between images. This can be seen more clearly in FIG. 5b.

Figure 6:
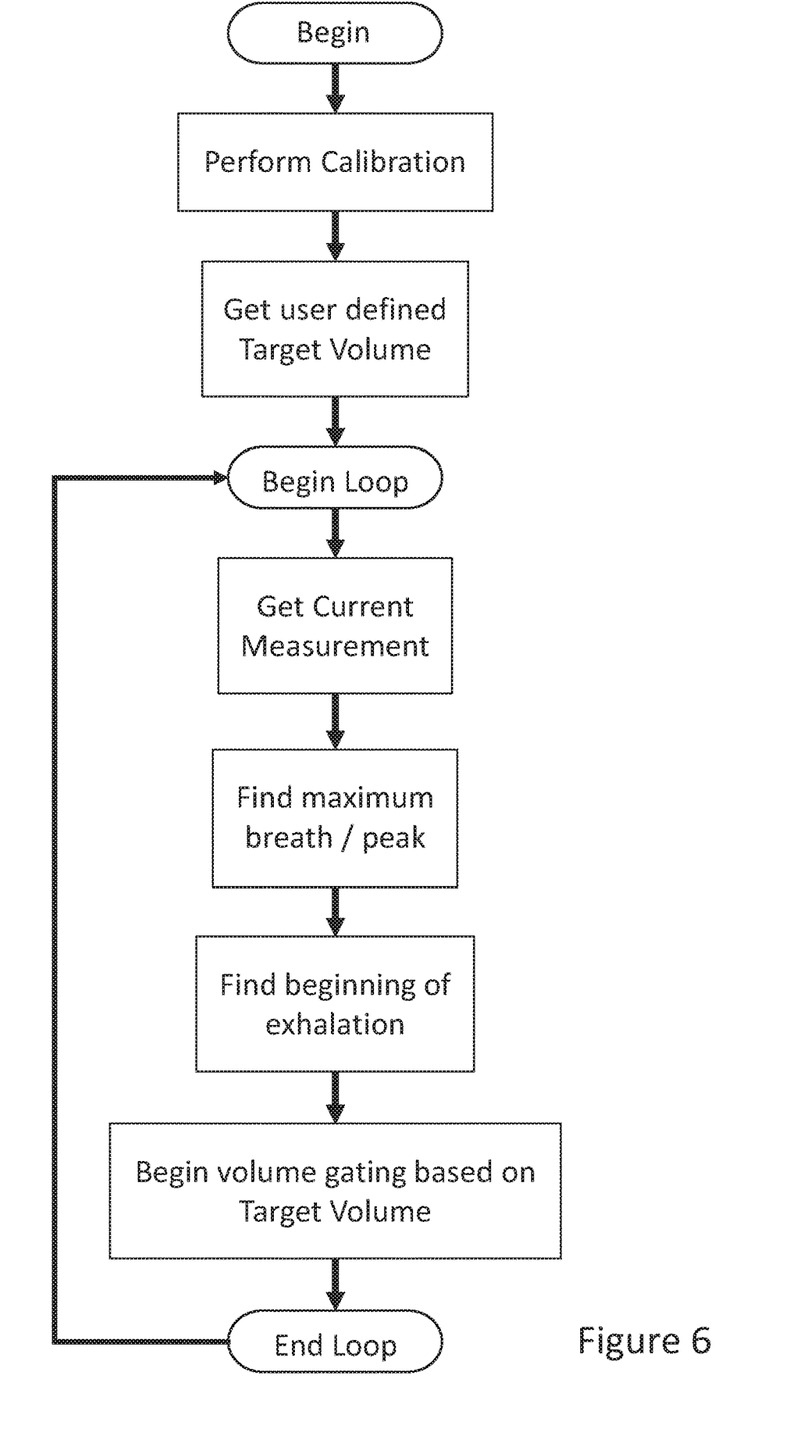
FIG. 6 is a flow chart summarizing the function of one embodiment of the application of a system according to the present invention.

FIG. 6 shows a flowchart of one particular embodiment of the application relating to this technology. This lists the processing steps that can occur for this technique to be used effectively.

Table 1 displays an example of the dose savings that can be achieved using this technique.

TABLE 1

Examples of Dose Saving for a Given Volume interval

| Volume | Number of frame | | Dose reduction |
|---|---|---|---|
| ΔL | Standard 30 fps | Triggered | Saving |
| 0.1 | 90 | 34 | 62% |
| 0.2 | 90 | 19 | 79% |
| 0.3 | 90 | 13 | 86% |
| 0.4 | 90 | 10 | 89% |

TABLE 1-continued

Examples of Dose Saving for a Given Volume interval

| Volume | Number of frame | | Dose reduction |
|---|---|---|---|
| ΔL | Standard 30 fps | Triggered | Saving |
| 0.5 | 90 | 9 | 90% |
| 0.6 | 90 | 7 | 92% |
| 0.7 | 90 | 6 | 93% |
| 0.8 | 90 | 6 | 93% |
| 0.9 | 90 | 5 | 94% |
| 1 | 90 | 4 | 96% |
| 1.1 | 90 | 4 | 96% |

Figure 7:
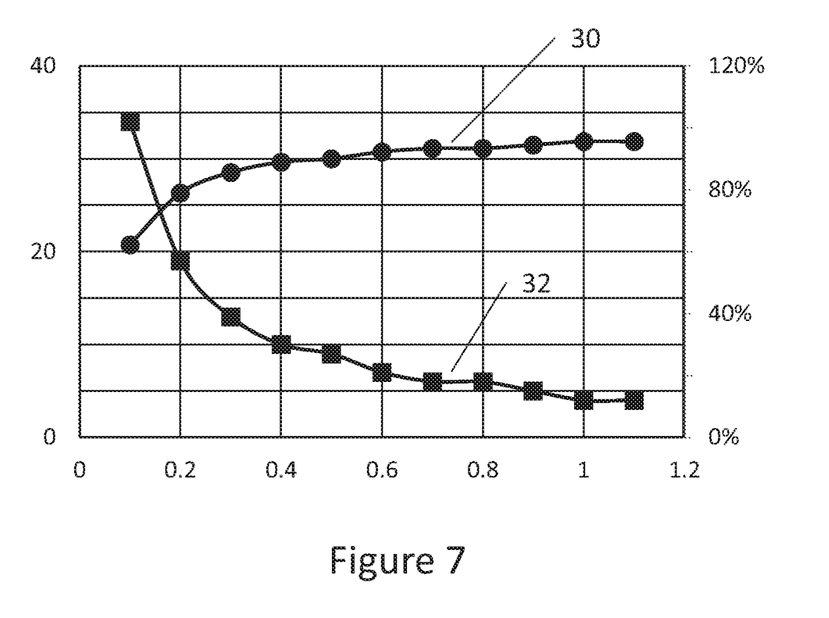
FIG. 7 is a graph illustrating radiation dose savings according to the present invention for preset volume change value for a system that is ordinarily run at 30 fps. This data can also be seen in Table 1.

FIG. 7 is a plot showing the dose reduction that is possible using the method of the present invention on a 30 frame per second imaging system as compared with imaging at a constant rate. The plot shows how the dose reduction changes (30) as the predetermined volume change of the lungs is set to different levels (triggered 32).

Figure 8A:
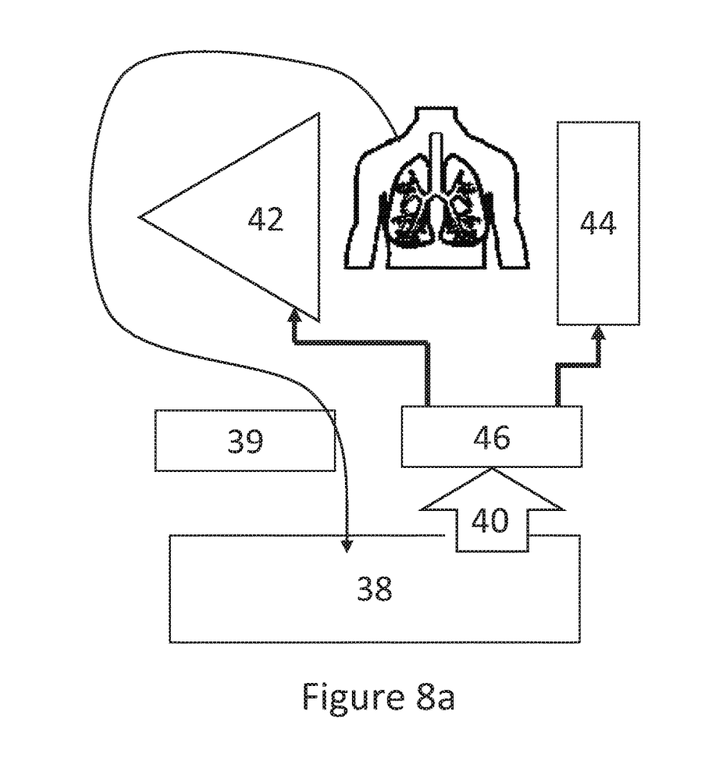
FIGS. 8a and 8b illustrate the system (FIG. 8a, also referred to herein as FIG. 8a) and apparatus (FIG. 8b also referred to herein as FIG. 8b) used for the method of this invention.
Figure 8B:
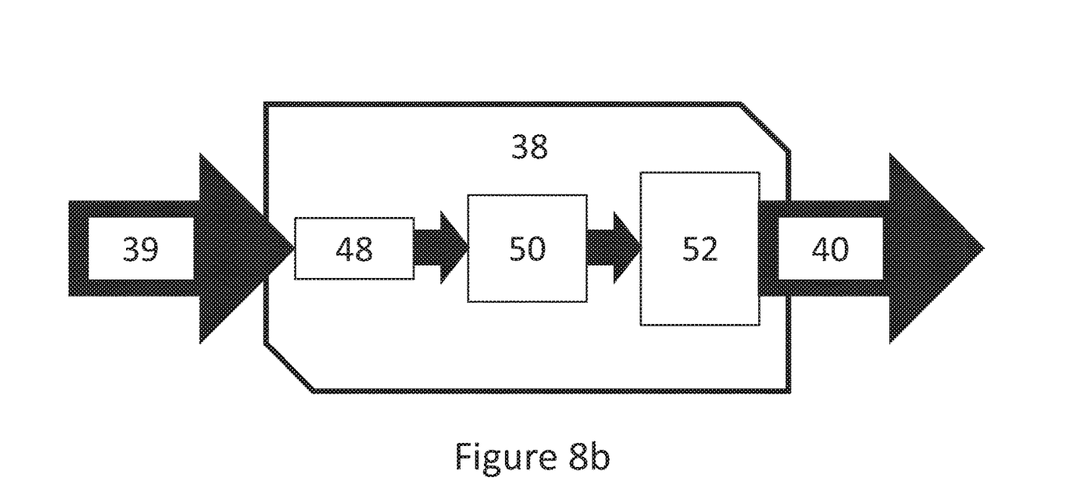

FIG. 8 shows the system and apparatus of the present invention. The physiological input (39) is sent from the patient located between the source (42) and the detector (44) to the sensor (48). The signal processing system (38) in FIG. 8a shows how a physiological parameter is used for controlling the timing of image acquisition of FIG. 8b. The sensor turns this physiological information into a parameter signal (50) that is then sent to the signal processing unit (52). The signal processing unit converts the signal to an appropriate trigger (40) that feeds into the imaging system controller (46). The signal processing may include some other input information from the user such as preset volume change value or an equation for a series of volume change values or another set of rules by which the input physiological information is to be converted to an appropriate triggering signal for the imaging system.

Typically, a CTXV scanner of this type comprises multiple energy sources and multiple detectors used simultaneously or in close temporal sequence. This current invention, when utilized in CTXV imaging (irrespective of the number of energy/detector pairs) includes application to imaging of animals and also application to imaging of humans. Due to the nature of CTXV technology often being utilized for direct measures of lung volume change, dramatic reductions in dose can be achieved for little or no loss of information gathered during a scan by using a volume based gating system.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

"Comprises/comprising" and "includes/including" when used in this specification is taken to specify the presence of stated features, integers, steps, or components but does not preclude the presence or addition of one or more other features, integers, steps, components, or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

What is claimed is:

1. A method of measuring an organ motion of an organ, the method comprising:
   monitoring for a plurality of occurrences of a same change of a parameter value corresponding to motion of the organ during a respiration cycle;
   acquiring a sequence of in vivo images of the organ between peak inhalation and peak expiration within the respiration cycle, wherein acquisition of each in vivo image in the sequence of in vivo images is separately triggered by a separate corresponding one of the plurality of occurrences of the same change of the parameter value; and
   measuring the organ motion between two or more of the in vivo images in the sequence of in vivo images.

2. The method of claim 1, wherein measuring the organ motion comprises:
   reconstructing a spatial velocity of motion from the in vivo images in the sequence of in vivo images.

3. The method of claim 1, wherein:
   acquiring the sequence of in vivo images of the organ between peak inhalation and peak expiration within the respiration cycle comprises acquiring a first sequence of in vivo images of the organ from a first perspective and acquiring a second sequence of in vivo images of the organ from a second perspective, and
   measuring the organ motion comprises subsequently, reconstructing a spatial velocity of organ motion from the first sequence of in vivo images and the second sequence of in vivo images.

4. The method of claim 1, wherein at least three in vivo images of the organ are acquired in the sequence of in vivo images.

5. The method of claim 1, wherein the same change of the parameter value is a predetermined value.

6. The method of claim 1, wherein the same change of the parameter value is a predetermined constant value.

7. The method of claim 1, wherein the in vivo images comprise in vivo fluoroscopy x-ray images.

8. The method of claim 1 wherein the organ is a lung.

9. The method of claim 1, wherein:
   monitoring for the plurality of occurrences of the same change in a parameter value comprises creating monitoring data that is fed in real time to an imaging control system, and
   acquisition of each in vivo image in the sequence of in vivo images is separately triggered by an actuation signal from the imaging control system.

10. The method of claim 9, wherein:
    acquiring the sequence of in vivo images of the organ between peak inhalation and peak expiration within the respiration cycle comprises acquiring a first sequence of in vivo images of the organ from a first perspective and acquiring a second sequence of in vivo images of the organ from a second perspective;
    acquisition of an in vivo image in the first sequence and a corresponding in vivo image in the second sequence is triggered by the same actuation signal from the imaging control system; and
    measuring the organ motion comprises subsequently, reconstructing a first spatial velocity of organ motion from the first sequence of in vivo images and reconstructing a second spatial velocity of organ motion from the second sequence of in vivo images.

11. The method of claim 1, wherein the same change of the parameter value corresponding to motion is a change in any one or any combination of shape, volume, flow, pressure, shear, displacement, orientation, or location of the organ.

12. The method of claim 11, wherein the same change of the parameter value corresponding to motion is a change in displacement of the organ.

13. A system comprising:
    one or more energy sources;
    one or more detectors configured to acquire in vivo images of an organ created by energy from the one or more energy sources passing through a subject intermediate the energy source and detector; and
    a signal processing system coupled to the one or more energy source and the one or more detectors and configured to:
        monitor for a plurality of occurrences of a same change of a parameter value corresponding to motion of the organ during a respiration cycle;
        acquire a sequence of in vivo images of the organ between peak inhalation and peak expiration within the respiration cycle, wherein acquisition of each in vivo image in the sequence of in vivo images is separately triggered by a separate corresponding one of the plurality of occurrences of the same change of the parameter value; and
        measure the organ motion between two or more of the in vivo images in the sequence of in vivo images.

14. The system of claim 13, wherein the signal processing system is configured to measure the organ motion by being configured to:
    reconstruct a spatial velocity of motion from the in vivo images in the sequence of in vivo images.

15. The system of claim 13, wherein:
    the signal processing system is configured to acquire a sequence of in vivo images of the organ between peak inhalation and peak expiration within the respiration cycle by being configured to acquire a first sequence of in vivo images of the organ from a first perspective and acquiring a second sequence of in vivo images of the organ from a second perspective, and
    the signal processing system is configured to measure the organ motion by being configured to subsequently, reconstruct a spatial velocity of organ motion from the first perspective based on the first sequence of in vivo images and the second sequence of in vivo images.

16. The system of claim 13, wherein the same change of the parameter value corresponding to motion is a change in any one or any combination of shape, volume, flow, pressure, shear, displacement, orientation, or location of the organ.

17. The system of claim 13, wherein at least three in vivo images of the organ are acquired in the sequence of in vivo images.

18. The system of claim 13, wherein:
the signal processing system is configured to monitor for the plurality of occurrences of the same change in a parameter value by being configured to create monitoring data in real time, and
the signal processing system is configured to separately trigger the acquisition of each in vivo image in the sequence of in vivo images in response to an actuation signal.

19. The system of claim 18, wherein:
the signal processing system is configured to acquire the sequence of in vivo images of the organ between peak inhalation and peak expiration within the respiration cycle by being configured to acquire a first sequence of in vivo images of the organ from a first perspective and acquire a second sequence of in vivo images of the organ from a second perspective, wherein acquisition of an in vivo image in the first sequence and a corresponding in vivo image in the second sequence is triggered by the same actuation signal from an imaging control system; and the signal processing system is configured to measure the organ motion by being configured to subsequently, reconstruct a spatial velocity of organ motion from the first sequence of in vivo images and the second sequence of in vivo images.

20. A non-transitory computer readable storage medium storing computer executable code, comprising instruction for causing an apparatus to:

monitor for a plurality of occurrences of a same change of a parameter value corresponding to motion of an organ during a respiration cycle;

acquire a sequence of in vivo images of the organ between peak inhalation and peak expiration within the respiration cycle, wherein acquisition of each in vivo image in the sequence of in vivo images is separately triggered by a separate corresponding one of the plurality of occurrences of the same change of the parameter value; and measure the organ motion between two or more of the in vivo images in the sequence of in vivo images.

* * * * *